(12) United States Patent
Irisawa et al.

(10) Patent No.: US 10,305,249 B2
(45) Date of Patent: May 28, 2019

(54) LASER APPARATUS

(71) Applicant: FUJIFILM Corporation, Tokyo (JP)

(72) Inventors: Kaku Irisawa, Kanagawa (JP); Tomoki Inoue, Kanagawa (JP); Atsushi Hashimoto, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 16/043,910

(22) Filed: Jul. 24, 2018

(65) Prior Publication Data

US 2018/0331496 A1 Nov. 15, 2018

Related U.S. Application Data

(63) Continuation of application No. PCT/JP2017/001467, filed on Jan. 18, 2017.

(30) Foreign Application Priority Data

Jan. 26, 2016 (JP) ................. 2016-012831

(51) Int. Cl.
*H01S 5/024* (2006.01)
*G01N 29/24* (2006.01)
(Continued)

(52) U.S. Cl.
CPC ......... *H01S 5/02407* (2013.01); *G01N 29/24* (2013.01); *G01N 29/2418* (2013.01);
(Continued)

(58) Field of Classification Search
CPC .. H01S 5/02407; H01S 3/0404; H01S 3/0405; H01S 3/024
See application file for complete search history.

(56) References Cited

U.S. PATENT DOCUMENTS

| 4,578,792 A | 3/1986 | Hoag | |
|---|---|---|---|
| 2005/0254537 A1* | 11/2005 | Su | H01S 5/02 372/43.01 |

(Continued)

FOREIGN PATENT DOCUMENTS

| GB | 2158635 A | 11/1985 |
|---|---|---|
| JP | 11-84992 A | 3/1999 |

(Continued)

OTHER PUBLICATIONS

International Preliminary Report on Patentability and the Written Opinion of the International Searching Authority (Forms PCT/IB/326, PCT/IB/373 and PCT/ISA/237), dated Aug. 9, 2018, for International Application No. PCT/JP2017/001467, along with an English translation.

(Continued)

*Primary Examiner* — Michael Carter
(74) *Attorney, Agent, or Firm* — Birch, Stewart, Kolasch & Birch, LLP

(57) ABSTRACT

In a laser apparatus, transmission of vibration, which is generated in a portion that generates a cooling gas flow, to a laser unit is suppressed, and heat generated from the laser unit is efficiently dissipated. A laser unit is housed inside a box-shaped housing having a plurality of faces. A frame supports a laser unit with a first mount interposed therebetween inside the housing. The frame has a through-hole penetrating from one face side to the other face side. A blower fan generates a flow of cooling gas for cooling the laser unit. The blower fan is attached to, for example, a second housing so as to face the laser unit. The cooling gas moves through the through-hole of the frame between the blower fan and the laser unit.

19 Claims, 6 Drawing Sheets

(51) Int. Cl.
- *H01S 3/00* (2006.01)
- *H01S 3/02* (2006.01)
- *H01S 3/042* (2006.01)
- *H05K 7/20* (2006.01)
- *H01S 5/022* (2006.01)

(52) U.S. Cl.
CPC .................. *H01S 3/00* (2013.01); *H01S 3/02* (2013.01); *H01S 3/042* (2013.01); *H01S 5/024* (2013.01); *H01S 5/0228* (2013.01); *H01S 5/02476* (2013.01); *H05K 7/20* (2013.01)

(56) References Cited

U.S. PATENT DOCUMENTS

| | | |
|---|---|---|
| 2016/0226214 A1 | 8/2016 | Ishii et al. |
| 2016/0349493 A1 | 12/2016 | Matsui et al. |

FOREIGN PATENT DOCUMENTS

| | | |
|---|---|---|
| JP | 2003-507893 A | 2/2003 |
| JP | 2008-21899 A | 1/2008 |
| JP | 2010-153198 A | 7/2010 |
| JP | 2015-111660 A | 6/2015 |
| JP | 2015-152831 A | 8/2015 |
| JP | 2016-112612 A | 6/2016 |

OTHER PUBLICATIONS

International Search Report (Form PCT/ISA/210), dated May 9, 2017, for International Application No. PCT/JP2017/001467, along with an English translation.

Extended European Search Report, dated Jan. 7, 2019, for European Application No. 17744036.9.

Japanese Office Action dated Mar. 26, 2019, for Japanese Patent Application No. 2017-564188, with an English translation.

* cited by examiner

LASER APPARATUS

CROSS-REFERENCE TO RELATED APPLICATIONS

This application is a continuation application of International Application No. PCT/JP2017/001467, filed Jan. 18, 2017, the disclosure of which is incorporated herein by reference in its entirety. Further, this application claims priority from Japanese Patent Application No. 2016-012831, filed Jan. 26, 2016, the disclosure of which is incorporated herein by reference in its entirety.

BACKGROUND

1. Technical Field

The present invention relates to a laser apparatus, and more particularly to a laser apparatus having a cooling mechanism.

2. Related Art

As a kind of image examination method capable of examining the state of the inside of the living body in a non-invasive manner, an ultrasound examination method is known. In ultrasound examination, an ultrasound probe capable of transmitting and receiving ultrasound waves is used. In a case where ultrasound waves are transmitted to a subject (living body) from the ultrasound probe, the ultrasound waves propagate through the living body and are reflected on the tissue interface. By receiving the reflected ultrasound waves using the ultrasound probe and calculating the distance based on the time until the reflected ultrasound waves return to the ultrasound probe, it is possible to image the state of the inside.

In addition, photoacoustic imaging for imaging the inside of the living body using the photoacoustic effect is known. In general, in photoacoustic imaging, pulsed laser light is emitted into the living body. In the living body, the living tissue absorbs the energy of the pulsed laser light, and ultrasound waves (photoacoustic waves) are generated by adiabatic expansion due to the energy. By detecting the photoacoustic waves using an ultrasound probe or the like and forming a photoacoustic image based on the detection signal, it is possible to visualize the inside of the living body based on the photoacoustic waves.

For measurement of photoacoustic waves, it is necessary to emit pulsed laser light with high intensity in many cases, and a solid state laser apparatus that performs Q switch pulse oscillation is used as a light source in many cases. The solid state laser apparatus has, for example, a laser rod (laser medium) and a flash lamp (excitation lamp) for exciting the laser rod. The laser apparatus has a Q switch for Q switch pulse oscillation. As a laser apparatus that can be used for photoacoustic measurement, a laser apparatus in which alexandrite crystal is used as a laser medium is disclosed in JP2015-111660A, for example. JP2015-111660A discloses that the volume of the alexandrite crystal is reduced to reduce the size of the laser apparatus.

Here, as the laser apparatus becomes smaller, the problem of heat generation becomes more serious. Accordingly, it is important to cool the laser apparatus efficiently. Regarding the cooling of a compact high-output laser apparatus, JP2008-21899A discloses a cooling structure in a laser oscillation apparatus that obtains output laser light by making light, which is emitted from a semiconductor laser, incident on an optical fiber for fiber laser as excitation light. The laser oscillation apparatus disclosed in JP2008-21899A has a semiconductor laser array that emits excitation laser light and an optical fiber for fiber laser, which has a laser active material and generates output laser light excited by the incident excitation laser light in a case where the excitation laser light is incident thereon. The laser oscillation apparatus is housed in an approximately box-shaped housing (casing), and is placed on a horizontal plane by leg portions.

The cooling structure disclosed in JP2008-21899A includes a semiconductor laser heat dissipating member for dissipating heat generated from the semiconductor laser array, a fiber laser heat dissipating member for dissipating heat generated from the optical fiber for fiber laser, and a cooling fan for blowing cooling air to the semiconductor laser heat dissipating member and the fiber laser heat dissipating member. The cooling fan is disposed so as to face the semiconductor laser heat dissipating member, so that the cooling air blown from the cooling fan hits the semiconductor laser heat dissipating member. The cooling air is guided to the fiber laser heat dissipating member through a guide member after hitting the semiconductor laser heat dissipating member. In JP2008-21899A, by using such a configuration, the semiconductor laser array and the optical fiber for fiber laser are cooled by the cooling fan.

Regarding the cooling of an optical system including a laser. JP1999-84992A (JP-H11-84992A) discloses a cooling structure in a holographic stereogram creating apparatus. The holographic stereogram creating apparatus disclosed in JP1999-84992A (JP-H11-84992A) includes an optical system that records interference fringes generated by object laser light and reference laser light on a recording medium as an element hologram, vibration absorption support means for supporting the absorption of vibration of at least the optical system with respect to the housing, and cooling means for cooling at least the optical system. The optical system includes a laser light source. The cooling means is configured to include a driving unit, such as a blower fan disposed on the housing side, and a duct formed of a non-rigid body provided between the driving unit and the optical system. In JP1999-84992A (JP-1411-84992A), since the absorption of vibration of the optical system including the laser light source with respect to the housing is supported on the vibration absorption support means, transmission of vibration caused by the rotation of a fan to the optical system is suppressed.

SUMMARY

In JP2008-21899A, the cooling fan is disposed on the side surface perpendicular to the mounting surface. The area of the side surface is narrower than the area of the bottom surface parallel to the mounting face. Accordingly, since the number of fans that can be disposed is limited, the cooling capacity is limited. In addition, in JP2008-21899A, there is also a problem that vibration generated from the cooling fan is transmitted to the semiconductor laser array.

In JP1999-84992A (JP-H11-84992A), since the absorption of vibration of the laser light source with respect to the housing is supported and the driving unit, such as a fan, is disposed on the housing side, vibration generated from the fan is hardly transmitted to the laser light source or the like. In JP1999-84992A (JP-H11-84992A), however, a blower fan is disposed at one end portion of the duct, and an exhaust fan is disposed at the other end portion. Therefore, the laser light source is cooled by cooling air flowing through the duct. In JP1999-84992A (JP-H11-84992A), since the cooling air flows only inside the duct, the volume of the cooling air is determined by the diameter (area) of the duct. For this reason, improvement in the cooling capacity is limited.

In view of the above circumstances, it is an object of the present invention to provide a laser apparatus capable of suppressing the transmission of vibration, which is generated in a portion that generates a cooling airflow, to a laser unit and of efficiently dissipating heat generated from the laser unit.

In order to achieve the aforementioned object, the present invention provides a laser apparatus comprising: a laser unit that is housed inside a box-shaped housing having a plurality of faces; a frame that supports the laser unit with a first mount interposed therebetween in the housing; and a cooling gas flow generation unit that is attached to a member different from the frame and generates a flow of cooling gas for cooling the laser unit. The cooling gas flow generation unit is disposed on a side of a face having a largest area or a face opposite to the face having the largest area, among a plurality of faces of the housing, so as to face the laser unit. The frame has a through-hole penetrating from one face, which is a face on a side where the laser unit is supported, to the other face. The cooling gas moves through the through-hole of the frame between the cooling gas flow generation unit and the laser unit.

The laser apparatus of the present invention may further comprise a substrate, the laser unit being mounted on one face of the substrate and a radiator that is attached to another face of the substrate which is opposite to the one face of the substrate.

In the above, it is preferable that the substrate is supported on the frame with the first mount interposed therebetween.

In a case where the laser apparatus has a configuration having a substrate on which the laser unit is mounted, the substrate may include a first portion on which the laser unit is mounted, a second portion rising from the first portion toward one face side on which the laser unit is mounted, and a third portion connected to the first portion through the second portion, and the substrate may be supported on the frame at the third portion with the first mount interposed between the frame and the third portion.

At least one of a transmission optical system, a coupling optical system, or an optical connector for connection with a probe for photoacoustic measurement may be further mounted on the substrate.

In the above, it is preferable that at least a part of the first portion of the substrate and/or at least a part of the radiator enters the through-hole of the frame.

The laser apparatus of the present invention may further comprise a heat conduction member that is connected to at least one of the laser unit or the substrate and transfers heat generated by the laser unit to the frame.

The heat conduction member described above may include a braided shield wire formed of a material having a higher heat conductivity than that of at least one of the laser unit or the substrate.

Alternatively, the heat conduction member may include a film formed of a material having a higher heat conductivity than that of at least one of the laser unit or the substrate.

In the laser apparatus of the present invention, at least a part of the cooling gas flow generation unit may enter the through-hole of the frame.

The laser apparatus of the present invention may further comprise a partition member that partitions a space inside the housing into a space in which the laser unit is present and a space through which the cooling gas flows.

The partition member may include an air filter or may include a film member, for example.

In the laser apparatus of the present invention, the housing may include a first housing portion and a second housing portion that are separable from each other, and each of the first housing portion and the second housing portion may be attached to the frame.

In the laser apparatus of the present invention, the frame may have a protruding portion that protrudes from the first housing portion and the second housing portion.

In the laser apparatus of the present invention, the second housing portion may have a vent hole through which the cooling gas passes, and the cooling gas flow generation unit may be attached to the second housing portion.

In the laser apparatus of the present invention, the frame is attached to the housing with a second mount interposed therebetween.

The laser apparatus of the present invention may further comprise a cooling gas flow generation unit support member that supports the cooling gas flow generation unit.

The cooling gas flow generation unit support member may be attached to an inside of the housing with a third mount interposed therebetween.

The laser apparatus of the present invention can suppress the transmission of vibration, which is generated in a portion that generates a cooling gas flow, to a laser unit and efficiently dissipate heat generated from the laser unit.

BRIEF DESCRIPTION OF THE DRAWINGS

Exemplary embodiments according to the technique of the present disclosure will be described in detail based on the following figures, wherein.

DETAILED DESCRIPTION

Figure 1:
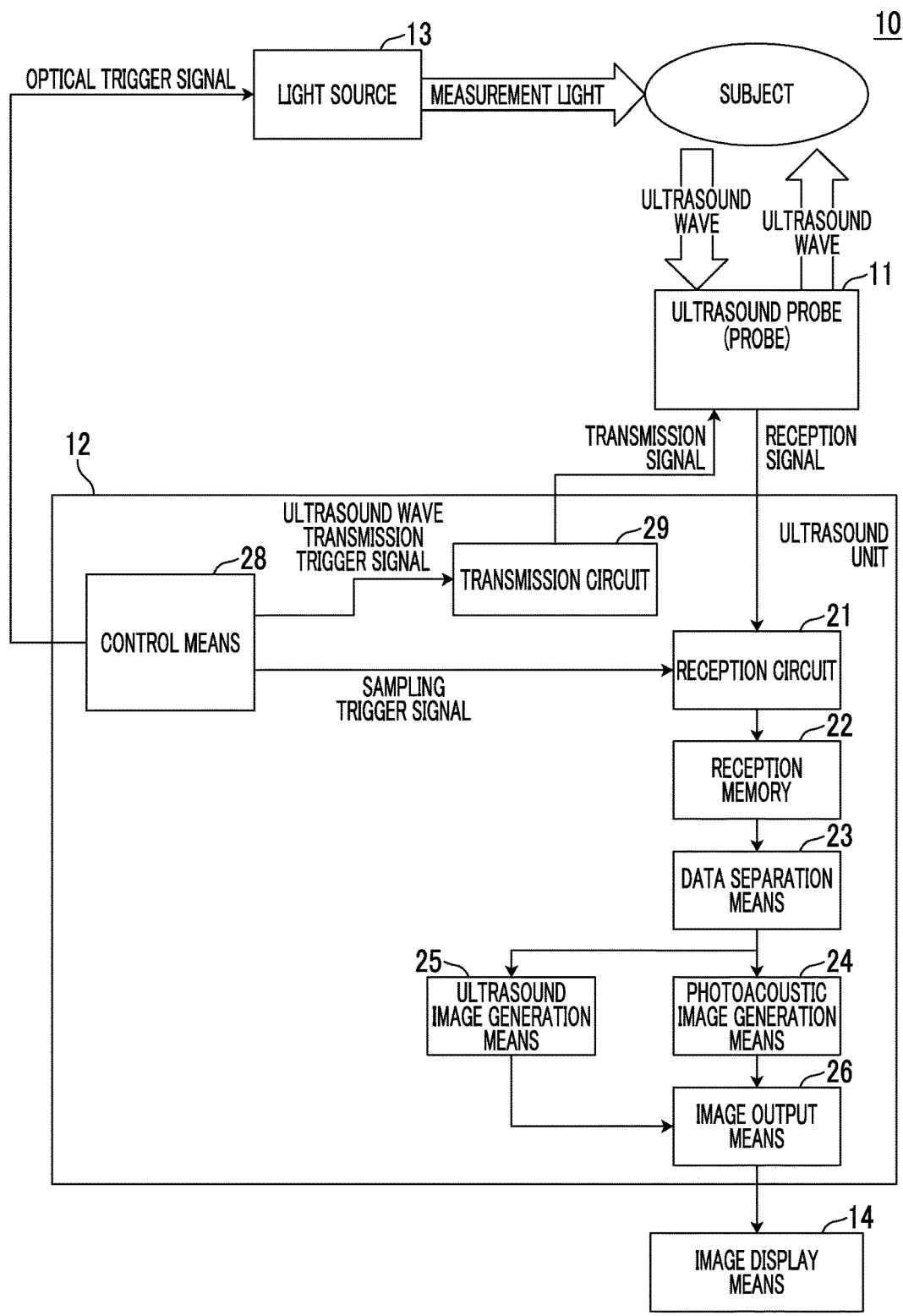
FIG. 1 is a block diagram showing a photoacoustic measurement apparatus including a laser apparatus according to a first embodiment of the present invention.

Hereinafter, embodiments of the present invention will be described in detail with reference to the diagrams. FIG. 1 shows a photoacoustic measurement apparatus including a laser apparatus according to a first embodiment of the present invention. A photoacoustic measurement apparatus 10 includes a probe (ultrasound probe) 11, an ultrasound unit 12, and a laser apparatus 13. In the embodiment of the present invention, an ultrasound wave is used as an acoustic wave. However, the acoustic wave is not limited to the ultrasound wave, and an acoustic wave having an audible frequency may be used as long as an appropriate frequency can be selected according to an examination target and/or measurement conditions, and the like.

The laser apparatus 13 emits measurement light to be emitted to a subject, such as a living tissue. The wavelength of the measurement light is appropriately set according to the living tissue of an observation target or the like. The laser apparatus 13 is, for example, a solid laser light source. Types of light sources are not particularly limited, and the laser apparatus 13 may be a laser diode light source (semiconductor laser light source), or may be an optical amplification type laser light source using a laser diode light source as a seed light source. The measurement light emitted from the laser apparatus 13 is guided to the probe 11 using, for example, light guide means, such as an optical fiber, and is emitted from the probe 11 toward the subject. The emission position of the measurement light is not particularly limited, and the measurement light may be emitted from a place other than the probe 11.

The probe 11 has a plurality of detector elements (ultrasound transducers) arranged in a one-dimensional manner, for example. The probe 11 detects photoacoustic waves generated in a case where a light absorber in the subject absorbs measurement light emitted toward the subject. In addition to the detection of photoacoustic waves, the probe 11 performs transmission of acoustic waves (ultrasound waves) to the subject and reception of reflected acoustic waves (reflected ultrasound waves) of the transmitted ultrasound waves. Transmission and reception of ultrasound waves may be performed at separate positions. For example, ultrasound waves may be transmitted from a position different from the probe 11, and reflected ultrasound waves of the transmitted ultrasound waves may be received by the probe 11. The type of the probe 11 is not particularly limited, and a linear probe may be used, or a convex probe or a sector probe may be used.

The ultrasound unit 12 has a reception circuit 21, a reception memory 22, data separation means 23, photoacoustic image generation means 24, ultrasound image generation means 25, image output means 26, control means 28, and a transmission circuit 29. The ultrasound unit 12 forms a signal processing apparatus. For example, the ultrasound unit 12 is formed as a computer apparatus having a processor, a memory, a bus, and the like. A program relevant to photoacoustic image generation is installed on the ultrasound unit 12, and at least some of functions of respective units in the ultrasound unit 12 are realized by opening the program.

The reception circuit 21 receives a detection signal output from the probe 11, and stores the received detection signal in the reception memory 22. Typically, the reception circuit 21 includes a low noise amplifier, a variable gain amplifier, a low pass filter, and an analog to digital converter (AD converter). The detection signal of the probe 11 is amplified by the low noise amplifier, and then the gain is adjusted according to the depth by the variable gain amplifier and a high-frequency component is cut by the low pass filter. Then, conversion into a digital signal is performed by the AD converter, and the digital signal is stored in the reception memory 22. The reception circuit 21 is formed by one integrated circuit (IC), for example.

The probe 11 outputs a detection signal of photoacoustic waves and a detection signal of reflected ultrasound waves, and detection signals (sampling data) of photoacoustic waves and reflected ultrasound waves after AD conversion are stored in the reception memory 22. The data separation means 23 reads the sampling data of the detection signal of photoacoustic waves from the reception memory 22, and transmits the sampling data to the photoacoustic image generation means 24. In addition, the data separation means 23 reads the sampling data of reflected ultrasound waves from the reception memory 22, and transmits the sampling data to the ultrasound image generation means (reflected acoustic wave image generation means) 25.

The photoacoustic image generation means 24 generates a photoacoustic image based on the detection signal of the photoacoustic wave detected by the probe 11. The generation of a photoacoustic image includes, for example, image reconstruction such as phase matching addition, detection, and logarithmic conversion. The ultrasound image generation means 25 generates an ultrasound image (reflected acoustic wave image) based on the detection signal of the reflected ultrasound wave detected by the probe 11. The generation of an ultrasound image also includes image reconstruction such as phase matching addition, detection, and logarithmic conversion. The image output means 26 outputs the photoacoustic image and the ultrasound image to image display means 14, such as a display device.

The control means 28 controls each unit in the ultrasound unit 12. For example, in the case of acquiring a photoacoustic image, the control means 28 transmits an optical trigger signal to the laser apparatus 13 so that the laser apparatus 13 emits measurement light. In addition, the control means 28 controls the sampling start timing of photoacoustic waves or the like by transmitting a sampling trigger signal to the reception circuit 21 in response to the emission of the measurement light.

In the case of acquiring an ultrasound image, the control means 28 transmits an ultrasound wave transmission trigger signal for giving an instruction of ultrasound wave transmission to the transmission circuit 29. In a case where the ultrasound wave transmission trigger signal is received, the transmission circuit 29 outputs a transmission signal, which is for transmitting ultrasound waves from the probe 11, to the probe 11, so that the ultrasound waves are transmitted from the probe 11. The probe 11 detects reflected ultrasound waves by performing a scan while shifting the acoustic line by one line at a time, for example. The control means 28 transmits a sampling trigger signal to the reception circuit 21 according to the timing of ultrasound wave transmission, thereby starting the sampling of reflected ultrasound waves.

Figure 2:
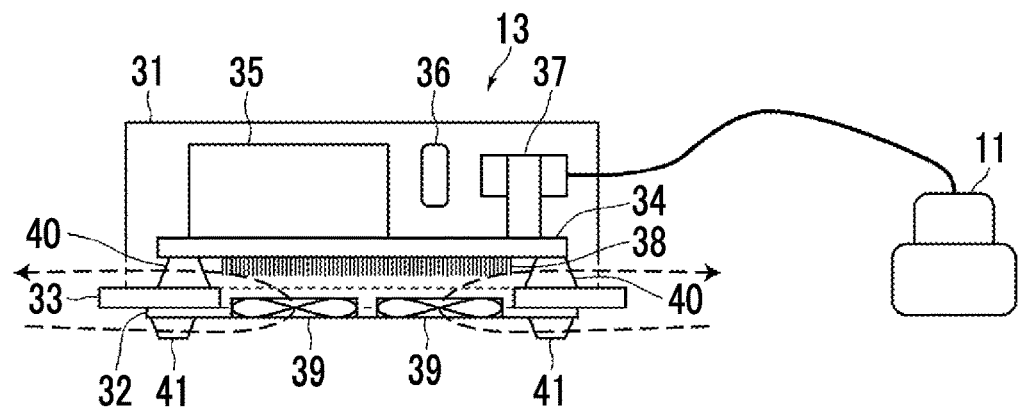
FIG. 2 is a cross-sectional view showing the inside of the laser apparatus according to the first embodiment of the present invention.
Figure 3:
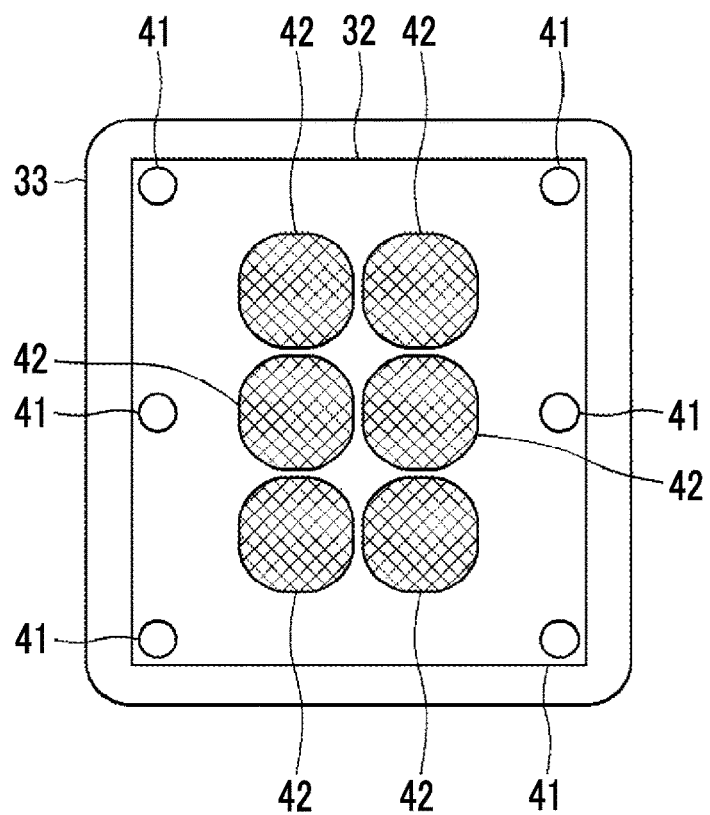
FIG. 3 is a diagram of the laser apparatus as viewed from the bottom face side.

FIG. 2 is a cross-sectional view showing the inside of the laser apparatus 13. In FIG. 2, a case where the measurement light emitted from the laser apparatus 13 is guided to the probe 11 using light guide means, such as an optical fiber, is described. In addition, a description relevant to the connection between the ultrasound unit and the probe will be omitted. FIG. 3 is a diagram of the laser apparatus 13 as viewed from the bottom face side. As shown in FIG. 2, the laser apparatus 13 has a laser unit 35, a transmission optical system 36, and a fiber connection optical system 37. The laser unit 35 is a unit that generates laser light. The laser unit 35 is configured as, for example, a diode pumped solid state (DPSS) laser light source. The laser unit 35 has, for example, an excitation laser diode light source, a laser rod, and a laser resonator optical system. The laser resonator optical system includes, for example, a mirror and a Q switch. The laser unit 35 may include a power supply for an excitation laser diode light source, a power supply for a Q switch, a transmission optical system, a coupling optical system, and/or an optical connector.

The laser unit 35 is housed inside a box-shaped housing (casing) having a plurality of faces. In the present embodiment, the housing includes an upper housing (first housing portion) 31 and a lower housing (second housing portion) 32 that are separable from each other. The upper housing 31 and the lower housing 32 are attached to a frame 33. The upper housing 31 and the lower housing 32 are fixed to the frame 33 by using, for example, a screw. In the present embodiment, the frame 33 has protruding portions that protrude from the upper housing 31 and the lower housing 32. By having the protruding portions, even in a case where the laser apparatus 13 hits on an obstacle, it is possible to suppress the transmission of impact to the housing unit. Leg portions 41 are attached to the lower housing 32 (also refer to FIG. 3), and the laser apparatus 13 is placed on a horizontal plane or the like with the lower housing 32 on the bottom. In the following description, for the sake of convenience, the face of the housing on the leg portion 41 side is referred to as a bottom face, and a face opposite thereto is referred to as a top face. A face perpendicular to the top face and the bottom face is referred to as a side face.

The laser light emitted from the laser unit 35 is incident on the fiber connection optical system 37 through the transmission optical system 36. The coupling optical system includes, for example, a lens and the like. The transmission optical system 36 may include a diffusion plate and/or a beam expander and the like. The transmission optical system 36 is not indispensable, and the laser apparatus 13 does not need to have the transmission optical system 36. The fiber connection optical system 37 includes, for example, a coupling optical system and an optical connector. An optical fiber extending from the probe 11 is connected to the optical connector of the fiber connection optical system 37. As the optical fiber, for example, a bundle fiber in which a plurality of element wires are bundled is used. The probe 11 includes, for example, a light guide plate for guiding the measurement light and/or a diffusion plate for diffusing the measurement light and the like, and emits the measurement light toward the subject through these plates.

The laser unit 35, the transmission optical system 36, and the fiber connection optical system 37 are mounted on an optical substrate 34. The optical substrate 34 is formed of a material having a high heat conductivity, such as an aluminum alloy, a magnesium alloy, a titanium alloy, or a copper alloy. A radiator 38 is attached to the face of the optical substrate 34 opposite to the face on which the laser unit 35 is mounted. The radiator 38 includes, for example, a plurality of radiating fins. The radiator 38 is formed of a material having a high heat conductivity, such as an aluminum alloy, a magnesium alloy, a titanium alloy, or a copper alloy.

The optical substrate 34 is attached to the frame 33 with a mount (first mount) 40 interposed therebetween. In other words, the frame 33 supports the laser unit 35 mounted on the optical substrate 34 through the mount 40. For the mount 40, for example, antivibration rubber is used. The frame 33 has a through-hole penetrating from one face, which is a face supporting the laser unit 35 (optical substrate 34), to the other face.

A blower fan 39 that is an example of a cooling gas flow generation unit is a fan for generating a flow of cooling gas (cooling gas flow) used for cooling the laser unit 35. The blower fan 39 is attached to a member different from the frame 33. The cooling gas flow generation unit is not limited thereto, and a blower or the like may be used. The blower fan 39 is disposed on a side of a face having the largest area or a face opposite to the face, among a plurality of faces of the housing of the laser apparatus 13, so as to face the laser unit 35. Here, the area of each of the plurality of faces of the housing means the area of each face in a case where each face is viewed from a direction perpendicular to the face. In other words, the area of each face is defined as the area of each face in a case where each face is projected on a plane parallel to the face.

In the present embodiment, the blower fan 39 is disposed in the lower housing 32 so as to face the optical substrate 34. For example, a total of six blower fans 39 are attached to the lower housing 32. The blower fan 39 blows cooling gas to the optical substrate 34, on which the laser unit 35 is mounted, through a through-hole of the frame 33. As shown in FIG. 3, the lower housing 32 has a vent hole, through which the cooling gas passes, at a portion where the blower fan 39 is disposed. The blower fan 39 sucks the cooling gas flow from the vent hole. The cooling gas sucked by the blower fan 39 is blown to the radiator 38 through the through-hole of the frame 33 as indicated by the broken line arrow in FIG. 2.

The heat generated by the laser unit 35 and the like reaches the radiator 38 through the optical substrate 34, and cooling gas is blown to the radiator 38 so that the laser unit 35 and the like are cooled. It is preferable that at least a part of the blower fan 39 enters the through-hole of the frame 33. In this case, since the distance between the blower fan and the radiator 38 can be shortened, it is possible to efficiently cool the laser unit 35. The cooling gas blown to the radiator 38 is discharged to the outside of the housing through an exhaust port provided in the upper housing 31.

In the present embodiment, the blower fan 39 is disposed on a side of a face having the largest area or a face opposite to the face, among a plurality of faces of the housing of the laser apparatus 13. In this case, it is possible to dispose a larger number of blower fans than in a case where the blower fan 39 is disposed on the other faces. Alternatively, it is possible to dispose the blower fan 39 having a larger size than in a case where the blower fan 39 is disposed on the other faces. In the present embodiment, since it is possible to dispose a large number of blower fans 39 and/or a large sized blower fan, it is possible to increase the amount of cooling gas that can be blown per unit time. As a result, it is possible to efficiently cool the laser unit 35.

In the present embodiment, the blower fan 39 is attached to a member different from the frame 33, for example, the lower housing 32. The blower fan 39 generates vibration in accordance with a rotation operation. Since the vibration generated in the blower fan 39 is transmitted to the frame 33 through the lower housing 32, it is possible to suppress the vibration of the frame 33 compared with a case where the blower fan 39 is directly attached to the frame 33. As a result, it is possible to suppress vibration transmitted from the frame 33 to the optical substrate 34 on which the laser unit 35 is mounted. In the present embodiment, the frame 33 supports the optical substrate 34 through the mount 40, such as antivibration rubber. By suppressing the vibration transmitted from the frame 33 to the optical substrate 34 using the mount 40, it is possible to further suppress the transmission of the vibration generated in the blower fan 39 to the laser unit 35.

In the present embodiment, the blower fan 39 is disposed so as to face the optical substrate 34. Since the frame 33 has a through-hole, the cooling gas flow blown by the blower fan 39 is sent to the radiator 38 attached to the optical substrate 34 through the through-hole. By providing a through-hole in the frame 33, the blower fan 39 can be provided at a position facing the optical substrate 34, so that the cooling gas flow can be blown from the position facing the optical substrate 34 to the optical substrate 34. In the case of adopting such a configuration, it is possible to efficiently apply the cooling gas flow to the optical substrate 34 (radiator 38), compared with a case of cooling through a duct. As a result, it is possible to improve the cooling efficiency while suppressing the transmission of vibration.

Figure 4:
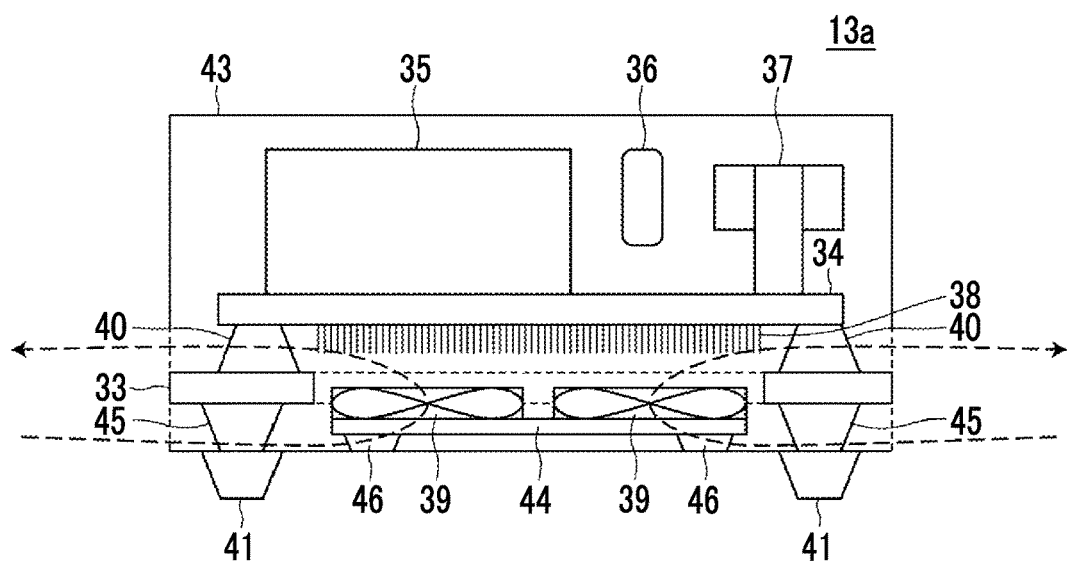
FIG. 4 is a cross-sectional view showing the inside of a laser apparatus according to a second embodiment of the present invention.

Next, a second embodiment of the present invention will be described. FIG. 4 is a cross-sectional view showing the inside of a laser apparatus according to the second embodiment of the present invention. In a laser apparatus 13a according to the present embodiment, the frame 33 is housed inside a housing 43, and the frame 33 does not have a protruding portion that protrudes from the housing to the outside unlike the laser apparatus 13 according to the first embodiment shown in FIG. 2. In addition, the frame 33 is attached to the housing 43 with a mount (second mount) 45 interposed therebetween.

In addition to the components of the laser apparatus 13 according to the first embodiment, the laser apparatus 13a according to the present embodiment further has a blower fan support member (cooling gas flow generation unit support member) 44 that supports the blower fan 39. The blower fan support member 44 is attached to the inside of the housing 43 with a mount (third mount) 46 interposed therebetween. As the blower fan support member 44, for example, a thin substrate formed of a metal material or a resin material is used.

In the laser apparatus 13a according to the present embodiment, instead of or in addition to providing a vent hole (air inlet) for sucking the cooling gas flow on the bottom face of the housing 43, an air inlet is provided on the side face of the housing 43. The cooling gas sucked into the housing 43 from the side face of the housing 43 is blown from the blower fan 39 to the radiator 38 through the through-hole of the frame 33 as indicated by the broken line arrow in FIG. 4. Also in the present embodiment, it is preferable that at least a part of the blower fan 39 enters the through-hole of the frame 33.

In the present embodiment, the blower fan 39 is attached to the blower fan support member 44. The vibration generated in the blower fan 39 is transmitted from the blower fan support member 44 to the housing 43 through the mount 46 and then transmitted to the frame 33 through the mount 45. In the present embodiment, since two mounts are interposed in the vibration transmission path from the blower fan 39 to the frame 33, there is an effect that vibration transmitted to the frame 33 can be suppressed compared with the first embodiment. Other effects are the same as in the first embodiment.

Figure 5:
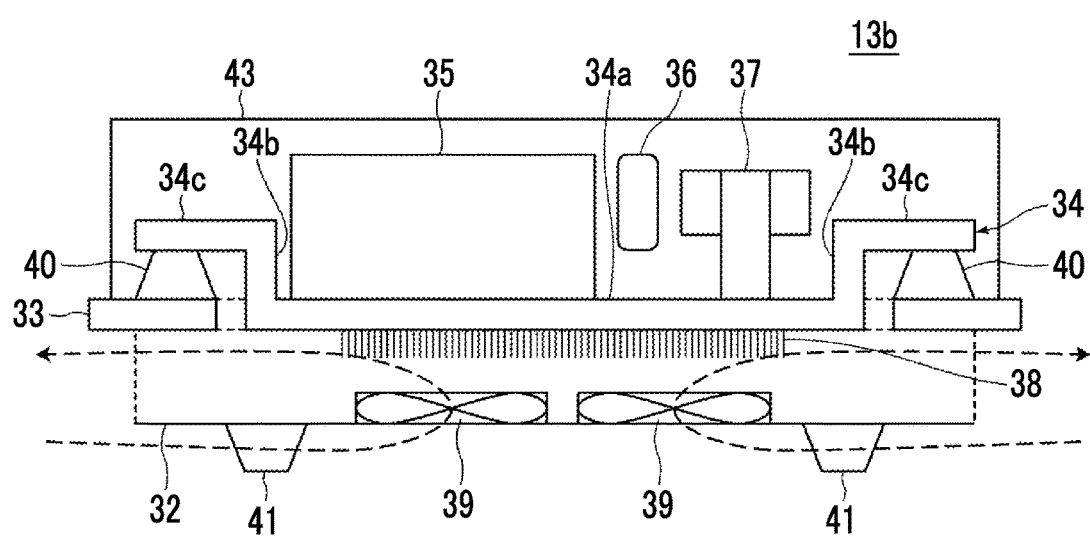
FIG. 5 is a cross-sectional view showing the inside of a laser apparatus according to a third embodiment of the present invention.

Subsequently, a third embodiment of the present invention will be described. FIG. 5 is a cross-sectional view showing the inside of a laser apparatus according to the third embodiment of the present invention. In a laser apparatus 13b according to the present embodiment, the optical substrate 34 includes a first portion 34a on which the laser unit 35 is mounted, a second portion 34b rising from the first portion toward a side of a face on which the laser unit 35 is mounted, and a third portion 34c connected to the first portion 34a through the second portion 34b. The first portion 34a and the third portion 34c are configured so as to be almost parallel to each other. The optical substrate 34 is supported on the frame 33 at the third portion 34c with the mount 40 interposed between the frame 33 and the third portion 34c. Others may be the same as in the first embodiment.

In the present embodiment, the optical substrate 34 has the second portion 34b that is bent from the first portion 34a of the optical substrate. Since the optical substrate 34 is bent toward the blower fan 39 side, the position of the first portion 34a of the optical substrate on which the laser unit 35 as a heat source is mounted can be moved to a position closer to the blower fan 39 than a connection location between the frame 33 and the optical substrate 34. In the present embodiment, it is preferable that at least a part of the first portion 34a of the optical substrate and/or at least a part of the radiator 38 attached thereto enters the through-hole of the frame 33.

In the laser apparatus 13b according to the present embodiment, an exhaust port is provided on the side face of the lower housing 32. The cooling gas sucked through the air inlet provided on the bottom face of the lower housing 32 is blown to the radiator 38 protruding from the through-hole of the frame 33 as indicated by the broken line arrow in FIG. 5. The cooling gas blown to the radiator 38 is discharged to the outside of the housing through an exhaust port provided on the side face of the lower housing 32.

In the present embodiment, the optical substrate 34 has the second portion 34b that is bent from the first portion 34a, on which the laser unit 35 is mounted, toward the side of the face on which the laser unit 35 is mounted. In addition, the optical substrate 34 is supported on the frame 33, at the third portion 34c that is bent from the second portion 34b toward the side opposite to the first portion 34a, with the mount 40 interposed between the optical substrate 34 and the frame 33. By adopting such a configuration, the distance between the radiator 38 and the blower fan 39 can be shortened compared with a case where the optical substrate 34 is not bent. It is possible to efficiently cool the heat generated by the laser unit 35 or the like by the shortened distance between the radiator 38 and the blower fan 39. In addition, compared with the first embodiment, the distance from the bottom face of the housing to the upper face can be shortened. Therefore, it is possible to reduce the size of the apparatus in the longitudinal direction. Other effects are the same as those in the first embodiment.

Figure 6:
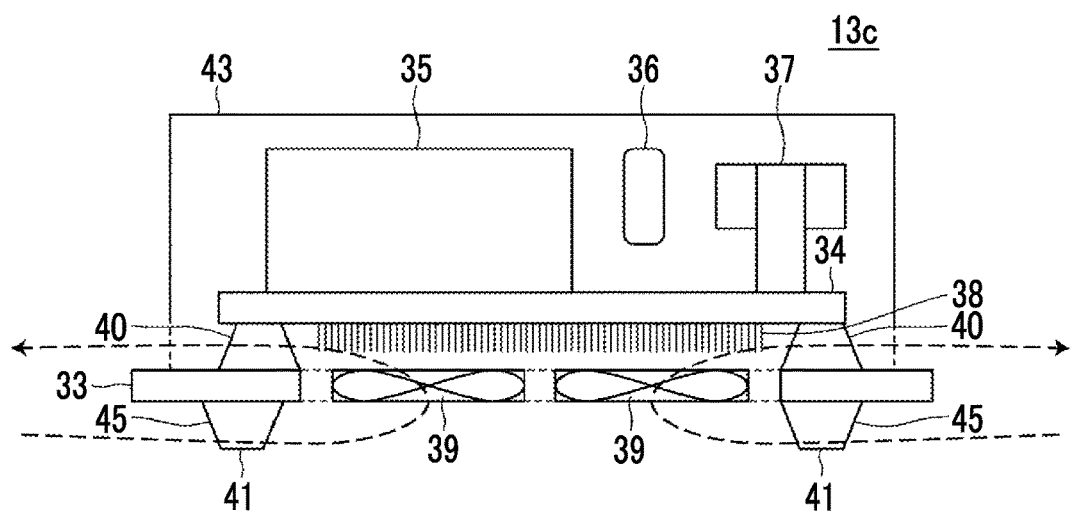
FIG. 6 is a cross-sectional view showing the inside of a laser apparatus according to a fourth embodiment of the present invention.

Subsequently, a fourth embodiment of the present invention will be described. FIG. 6 is a cross-sectional view showing the inside of a laser apparatus according to the fourth embodiment of the present invention. A laser apparatus 13c according to the present embodiment does not have the lower housing 32 (refer to FIG. 2), unlike the laser apparatus 13 according to the first embodiment shown in FIG. 2. In the present embodiment, the blower fan 39 is attached to the through-hole of the frame 33. Others may be the same as in the first embodiment.

In the laser apparatus 13c according to the present embodiment, as indicated by the broken line arrow in FIG. 6, the cooling gas is blown from the blower fan 39 attached to the through-hole of the frame 33 to the radiator 38. The cooling gas blown to the radiator 38 is discharged to the outside of the housing 43 through an exhaust port provided on the side face of the housing 43.

In the present embodiment, vibration generated in the blower fan 39 is transmitted to the frame 33 without passing through a mount formed of antivibration rubber or the like. Therefore, compared with the first embodiment in which the mount 40 (refer to FIG. 2) is interposed in the vibration transmission path from the blower fan 39 to the frame 33, there is a possibility that the vibration transmitted to the laser unit 35 will increase. However, similar to those described in the first embodiment, it is possible to obtain the effect that the laser unit 35 can be efficiently cooled and the effect that the cooling efficiency can be more improved than in the case of cooling through a duct.

Figure 7:
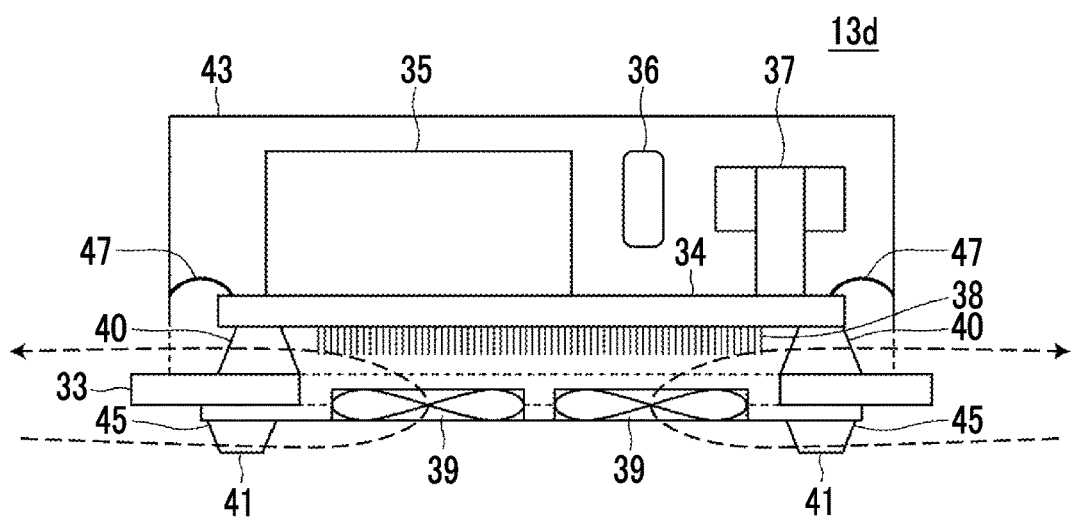
FIG. 7 is a cross-sectional view showing the inside of a laser apparatus according to a fifth embodiment of the present invention.
Figure 8:
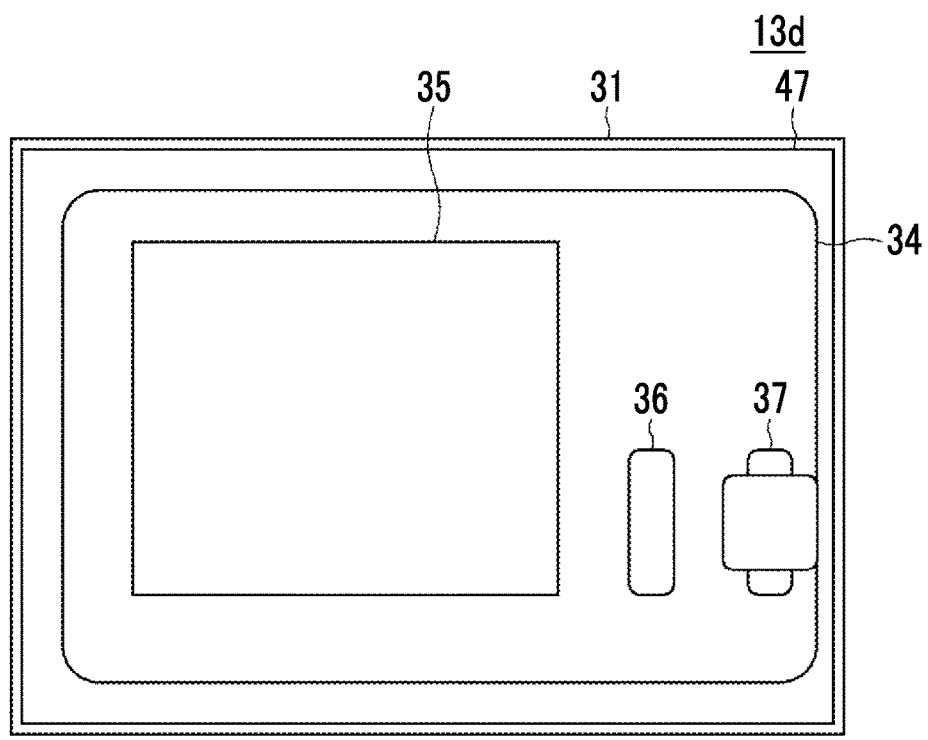
FIG. 8 is a diagram of the inside of the laser apparatus as viewed from the upper face side of the housing.

Next, a fifth embodiment of the present invention will be described. FIG. 7 is a cross-sectional view showing the inside of a laser apparatus according to the fifth embodiment of the present invention. A laser apparatus 13d according to the present embodiment has a partition member 47 in addition to the configuration of the laser apparatus according to the first embodiment shown in FIG. 2. The partition member 47 connects the optical substrate 34 and the inner wall of the upper housing 31 to each other. FIG. 8 is a diagram of the inside of the laser apparatus 13d as viewed from the upper face side of the housing. As shown in the diagram, the partition member 47 connects the optical substrate 34 and the inner wall of the upper housing 31 to each other over the entire circumference of the optical substrate 34. Others may be the same as in the first embodiment.

In the laser apparatus 13d, as indicated by the broken line arrow in FIG. 7, the cooling gas flow is sucked into the housing from the bottom face of the lower housing 32 and is discharged to the outside of the housing from the side face of the upper housing 31. The partition member 47 partitions the space inside the housing into a space in which the laser unit 35 is present and a space through which the cooling gas flows. The partition member 47 includes, for example, an air filter that allows the cooling gas flow to pass therethrough but does not allow floating dust and the like to pass therethrough. As the air filter, for example, a high efficiency particulate air filter (HEPA filter) can be used. The partition member 47 may include a film member that allows neither the cooling gas flow nor the floating dust to pass therethrough. As the film member, for example, a thin film tape or a thin film sheet, such as an aluminum tape, a copper tape, a polyimide film, or a polytetrafluoroethylene (PTFE) sheet, can be used.

In the present embodiment, partitioning into a space in which the laser unit 35 is present and a space through which the cooling gas flows is made by the partition member 47. In a case where the partition member 47 is not present, floating dust and the like contained in the cooling gas may enter the space in which the laser unit 35 is present. Since partitioning into a space in which the laser unit 35 is present and a space through which the cooling gas flows is made by the partition member 47, it is possible to prevent floating dust from entering the space in which the laser unit 35 is present inside the housing. In addition, in a case where an air filter and/or a film member is used as the partition member 47, even in a case where an impact is applied to the housing, there is an effect that transmission of the impact to the optical substrate 34 can be suppressed. Other effects are the same as in the first embodiment.

Figure 9:
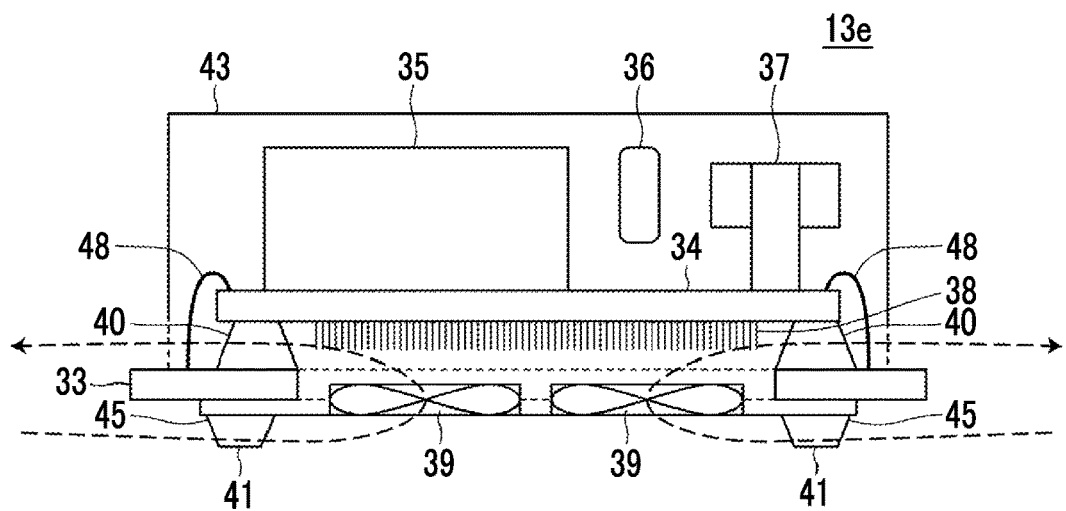
FIG. 9 is a cross-sectional view showing the inside of a laser apparatus according to a sixth embodiment of the present invention.

Subsequently, a sixth embodiment of the present invention will be described. FIG. 9 is a cross-sectional view showing the inside of a laser apparatus according to the sixth embodiment of the present invention. A laser apparatus 13e according to the present embodiment has a heat conduction member 48 in addition to the configuration of the laser apparatus according to the first embodiment shown in FIG. 2. The heat conduction member 48 connects the frame 33 and at least one of the laser unit 35 or the optical substrate 34 to each other. The heat conduction member 48 transfers heat generated by the laser unit 35 and the like to the frame 33. Others may be the same as in the first embodiment.

The heat conduction member 48 is formed of a material having a higher heat conductivity than that of at least one of the laser unit 35 or the optical substrate 34. By using a material having a high heat conductivity for the heat conduction member 48, heat can be transferred to the frame 33 from a portion where at least one of the laser unit 35 or the optical substrate 34 is connected to the heat conduction member 48. The heat conduction member 48 includes, for example, a braided shield wire. The heat conduction member 48 may include a film formed of a material having a high heat conductivity. For the film formed of a material having a high heat conductivity, for example, an aluminum tape, a copper tape, and a graphite sheet can be used.

In the present embodiment, heat generated from the laser unit 35 and the like is transferred to the frame 33 by using the heat conduction member 48. In the present embodiment, since the heat is transferred from the laser unit 35 and/or the optical substrate 34 to the frame 33 in addition to cooling the laser unit 35 by blowing the cooling gas flow, the laser unit 35 can be cooled more efficiently. Other effects are the same as those in the first embodiment.

The embodiments described above can be appropriately combined. For example, in the laser apparatuses according to the third, fifth, and sixth embodiments, similarly to the laser apparatus 13a (refer to FIG. 4) according to the second embodiment, a configuration in which the frame 33 is housed inside the housing 43 may be adopted. Alternatively, a configuration in which the blower fan support member 44 supports the blower fan 39 may be adopted. In addition, the laser apparatus according to each of the second, third, fourth, fifth, and sixth embodiments may adopt the configuration described in the third embodiment in which the optical substrate 34 has the first portion 34a, the second portion 34b, and the third portion 34c.

Figure 10:
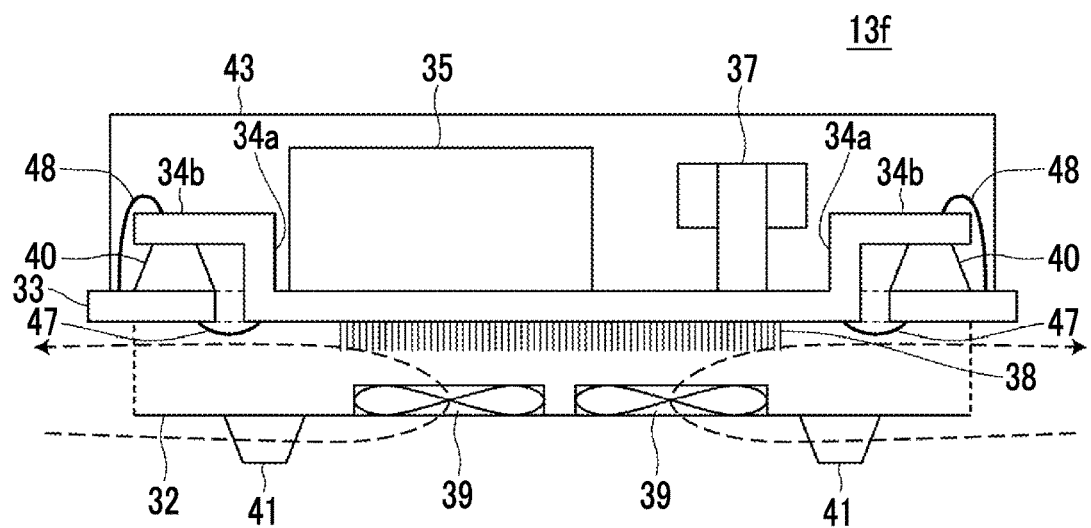
FIG. 10 is a cross-sectional view showing the inside of a laser apparatus according to a modification example.

The fifth and sixth embodiments may be combined so that the laser apparatus has both the partition member 47 and the heat conduction member 48. FIG. 10 is a cross-sectional view showing the inside of a laser apparatus according to a modification example. The configuration of a laser apparatus 13f according to the modification example is a configuration obtained by adding the partition member 47 described in the fifth embodiment and the heat conduction member 48 described in the sixth embodiment to the configuration of the laser apparatus 13b according to the third embodiment shown in FIG. 5. In the laser apparatus 13f according to the modification example, in addition to the effect described in the third embodiment, the effect described in the fifth embodiment and the effect described in the sixth embodiment are obtained.

In the above description, the laser apparatus according to the modification example in which the partition member 47 and the heat conduction member 48 are added to the configuration of the laser apparatus 13b according to the third embodiment has been described. However, it is also possible to adopt a configuration in which the partition member 47 and the heat conduction member 48 are added to the configurations of the laser apparatuses according to the other embodiments. For example, a configuration in which the partition member 47 and the heat conduction member 48 are added to the configuration of the laser apparatus 13a according to the second embodiment shown in FIG. 4 can be adopted, or a configuration in which the partition member 47 and the heat conduction member 48 are added to the configuration of the laser apparatus 13c according to the fourth embodiment shown in FIG. 6 can be adopted.

In each of the embodiments described above, the radiator 38 is attached to the optical substrate 34. However, the invention is not limited thereto, and the optical substrate 34 and the radiator 38 may be integrally formed. In addition, the radiator 38 is not limited to being attached to the flat substrate face of the optical substrate 34, and the radiator 38 may enter the optical substrate 34.

In each of the embodiments described above, an example has been described in which air is sucked into the housing from the outside of the housing and the cooling gas is blown from the blower fan 39 to the radiator 38. However, the flow direction of the cooling gas may be reversed. That is, a flow of the cooling gas may be generated from the inside of the housing to the outside using the blower fan 39, so that the heat of the radiator 38 is discharged to the outside of the housing through the blower fan 39. Even in this case, it is possible to obtain the same effects as those described in each of the above embodiments with respect to the cooling of the laser unit 35.

In each of the embodiments described above, an example in which the laser apparatus 13 is used in the photoacoustic measurement apparatus 10 has been described. However, the present invention is not limited thereto. The laser apparatus according to each of the above-described embodiments may be used in an apparatus different from the photoacoustic measurement apparatus 10.

While the present invention has been described based on the preferred embodiments, the laser apparatus of the present invention is not limited only to the above embodiments, and various modifications and changes in the configurations of the above embodiments are also included in the range of the present invention.

What is claimed is:

1. A laser apparatus, comprising:
   a laser unit that is housed inside a box-shaped housing having a plurality of faces;
   a frame that supports the laser unit with a first mount interposed therebetween in the housing; and
   a cooling gas flow generation unit that is attached to a member different from the frame and generates a flow of cooling gas for cooling the laser unit,
   wherein the cooling gas flow generation unit is disposed facing the laser unit and on a side of a face having a largest area or a face opposite to the face having the largest area among the plurality of faces of the housing,
   the frame has a through-hole penetrating from one face, which is a face on a side where the laser unit is supported, to the other face, and
   the cooling gas moves through the through-hole of the frame between the cooling gas flow generation unit and the laser unit.

2. The laser apparatus according to claim 1, further comprising:
   a substrate, the laser unit being mounted on one face of the substrate; and
   a radiator that is attached to another face of the substrate which is opposite to the one face of the substrate.

3. The laser apparatus according to claim 2,
   wherein the substrate is supported on the frame with the first mount interposed therebetween.

4. The laser apparatus according to claim 3,
   wherein the substrate includes a first portion on which the laser unit is mounted, a second portion rising from the first portion toward the one face side on which the laser unit is mounted, and a third portion connected to the first portion through the second portion, and the substrate is supported on the frame at the third portion with the first mount interposed between the frame and the third portion.

5. The laser apparatus according to claim 4,
   wherein at least a part of the first portion of the substrate and/or at least a part of the radiator enters the through-hole of the frame.

6. The laser apparatus according to claim 2,
   wherein at least one of a transmission optical system, a coupling optical system, or an optical connector for connection with a probe for photoacoustic measurement is further mounted on the substrate.

7. The laser apparatus according to claim 2, further comprising:
   a heat conduction member that is connected to at least one of the laser unit or the substrate and transfers heat generated by the laser unit to the frame.

8. The laser apparatus according to claim 7,
   wherein the heat conduction member includes a braided shield wire formed of a material having a higher heat conductivity than that of at least one of the laser unit or the substrate.

9. The laser apparatus according to claim 7,
   wherein the heat conduction member includes a film formed of a material having a higher heat conductivity than that of at least one of the laser unit or the substrate.

10. The laser apparatus according to claim 1,
    wherein at least a part of the cooling gas flow generation unit enters the through-hole of the frame.

11. The laser apparatus according to claim 1, further comprising:
    a partition member that partitions a space inside the housing into a space in which the laser unit is present and a space through which the cooling gas flows.

12. The laser apparatus according to claim 11,
    wherein the partition member includes an air filter.

13. The laser apparatus according to claim 11,
    wherein the partition member includes a film member.

14. The laser apparatus according to claim 1,
    wherein the housing includes a first housing portion and a second housing portion that are separable from each other, and
    each of the first housing portion and the second housing portion is attached to the frame.

15. The laser apparatus according to claim 14,
    wherein the frame has a protruding portion that protrudes from the first housing portion and the second housing portion.

16. The laser apparatus according to claim 15,
    wherein the second housing portion has a vent hole through which the cooling gas passes, and
    the cooling gas flow generation unit is attached to the second housing portion.

17. The laser apparatus according to claim 1,
    wherein the frame is attached to the housing with a second mount interposed therebetween.

18. The laser apparatus according to claim 17, further comprising:
    a cooling gas flow generation unit support member that supports the cooling gas flow generation unit.

19. The laser apparatus according to claim 18,
    wherein the cooling gas flow generation unit support member is attached to an inside of the housing with a third mount interposed therebetween.

* * * * *